United States Patent
Mandelbaum

(10) Patent No.: US 7,105,001 B2
(45) Date of Patent: Sep. 12, 2006

(54) SURGICAL METHOD AND COMPOSITION UTILIZING SUBMUCOSAL TISSUE TO PREVENT INCISIONAL HERNIAS

(76) Inventor: Jon A. Mandelbaum, 6450 Harting Overlook, Indianapolis, IN (US) 46237

( * ) Notice: Subject to any disclaimer, the term of this patent is extended or adjusted under 35 U.S.C. 154(b) by 0 days.

(21) Appl. No.: 10/851,358

(22) Filed: May 20, 2004

(65) Prior Publication Data

US 2005/0049638 A1    Mar. 3, 2005

Related U.S. Application Data

(60) Provisional application No. 60/472,797, filed on May 21, 2003.

(51) Int. Cl.
 *A61B 17/08* (2006.01)
 *A61B 19/00* (2006.01)
(52) U.S. Cl. ............. 606/151; 606/139; 606/148; 606/224; 128/898
(58) Field of Classification Search .......... 606/151, 606/139–158, 222–233, 213, 215, 216
See application file for complete search history.

(56) References Cited

U.S. PATENT DOCUMENTS

| | | | | |
|---|---|---|---|---|
| 2,748,774 | A | * 6/1956 | Novak | 606/229 |
| 4,902,508 | A | 2/1990 | Badylak et al. | |
| 4,956,178 | A | 9/1990 | Badylak et al. | |
| 5,281,422 | A | 1/1994 | Badylak et al. | |
| 5,290,217 | A | * 3/1994 | Campos | 600/37 |
| 5,433,996 | A | 7/1995 | Kranzler et al. | 442/40 |
| 5,554,389 | A | 9/1996 | Badylak et al. | |
| 5,711,969 | A | * 1/1998 | Patel et al. | 424/551 |
| 5,733,337 | A | * 3/1998 | Carr et al. | 435/325 |
| 5,743,917 | A | * 4/1998 | Saxon | 128/898 |
| 5,755,791 | A | * 5/1998 | Whitson et al. | 623/1.1 |
| 5,791,352 | A | * 8/1998 | Reich et al. | 128/898 |
| 5,955,110 | A | 9/1999 | Patel et al. | |
| 6,099,567 | A | 8/2000 | Badylak et al. | |
| 6,165,202 | A | * 12/2000 | Kokish et al. | 606/230 |
| 6,197,036 | B1 | * 3/2001 | Tripp et al. | 606/151 |
| 6,206,931 | B1 | 3/2001 | Cook et al. | |

(Continued)

FOREIGN PATENT DOCUMENTS

WO    WO02078568    10/2002

OTHER PUBLICATIONS

Medscape Abstract, "Use of polypropylene mesh in midline incision closure following by-pass surgery reduces the risk of postoperative hernia", abstracting Langenbecks Arch. Surg. Nov. 2002:387(7-8):294-7.

*Primary Examiner*—Glenn K. Dawson
(74) *Attorney, Agent, or Firm*—Randall J. Knuth

(57) ABSTRACT

A small intestine submucosa mesh is adapted for use in surgical abdominal closure routines. The submucosa mesh is incorporated into the normal surgical protocol for abdominal closure procedures. The submucosa mesh is applied to the abdominal incision area and maintains and enhances the stability and integrity of the abdominal wall closure, thereby preventing the onset or occurrence of incisional hernias. The submucosa mesh can also be applied to surgical closure procedures involving treatment of a hernia defect, such as an incisional hernia or other non-incisional hernia. The submucosa construct can also be adapted for use as a suturing component or bioretention suture. The submucosa construct can be adapted for use as part of a surgical strategy to facilitate wound healing, regeneration, reconstruction, and replacement of anatomical structures, such as tissues and organs.

2 Claims, 3 Drawing Sheets

U.S. PATENT DOCUMENTS

| | | |
|---|---|---|
| 6,355,065 B1 * | 3/2002 | Gabbay .................... 623/11.11 |
| 6,475,232 B1 | 11/2002 | Babbs et al. |
| 2002/0103542 A1 * | 8/2002 | Bilbo ...................... 623/23.72 |
| 2003/0074021 A1 | 4/2003 | Morriss et al. |
| 2004/0006353 A1 | 1/2004 | Bosley et al. |

* cited by examiner

SURGICAL METHOD AND COMPOSITION UTILIZING SUBMUCOSAL TISSUE TO PREVENT INCISIONAL HERNIAS

CONTINUING DATA

This application hereby claims the benefit under Title 35, United States Codes § 119 (e) of any U.S. application Ser. No. 60/472,797 filed May 21, 2003, and is hereby incorporated by reference.

BACKGROUND OF THE INVENTION

1. Field of the Invention

The present invention relates generally to surgical procedures and compositions suitable for use in surgical applications, and, more particularly, to the formation of a tissue graft construct employing a small intestine submucosa mesh and its use in various surgical protocols, such as abdominal closure incisions, hernia defect repair, and internal bioretention sutures.

2. Description of the Related Art

Medical procedures involving peritoneal access into the abdominal wall cavity typically need to address the incidence of incisional hernias as one possible future complication. It is known that 7% of patients having abdominal incisions will develop incisional hernias. This percentage increases with smoking, obesity, wound infections, malnourished patients, diabetes, and other known conditions.

A need exists to develop a surgical technology that mitigates the incidence of post-operative incisional hernias, which is cost effective, readily amenable to use in routine abdominal closure regimens, and does not necessitate any additional surgical procedures beyond what is already warranted by the abdominal closure specification.

Additionally, current retention sutures, such as those typically employed to facilitate an abdominal closure or otherwise treat an incision, are very painful to the patient since they are external and tend to pull on the abdominal wall. The conventional sutures also tend to dig into the skin, causing irritation, infection and unsightly scars.

A need therefore exists to develop a suturing technology that overcomes these problems.

SUMMARY OF THE INVENTION

According to the present invention, there is provided a small intestine submucosa mesh adapted for use in surgical abdominal closure routines. In particular, application of the submucosa mesh is incorporated into the surgical protocol for conventional abdominal closure procedures. This application of the submucosa mesh is especially adapted as a preventative measure to maintain, enhance, improve, and fortify the stability and integrity of the abdominal wall closure and thereby prevent the onset or occurrence of incisional hernias. The submucosa mesh provides particular long-term strength to the fascial closure.

In another form, the submucosa mesh can be applied to surgical closure procedures involving treatment of a hernia defect, such as an incisional hernia or other non-incisional hernia.

In another form, the submucosa construct can be adapted for use as a suturing component. In one exemplary configuration, the submucosa suture is arranged as a bioretention suture.

In another form, a submucosa construct is developed that can be used as part of a surgical strategy to facilitate wound healing, regeneration, reconstruction, and replacement of anatomical structures, such as tissues and organs.

One advantage of the present invention is that the submucosa mesh construct is readily adapted and amenable for direct use in the standard abdominal wall closure and/or suturing protocols found in conventional surgical procedures.

Another advantage of the present invention is that the use of the submucosa mesh construct in abdominal wall closure procedures provides a significant deterrent to the subsequent onset and occurrence of incisional hernias.

A further advantage of the invention is that the submucosa mesh construct can be readily adapted for use in surgical procedures addressing the treatment of hernia defects.

Another advantage of the invention is that the submucosa article construct can be adapted for use as an effective implantable internal suture to thereby eliminate the conventional requirement of external sutures.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
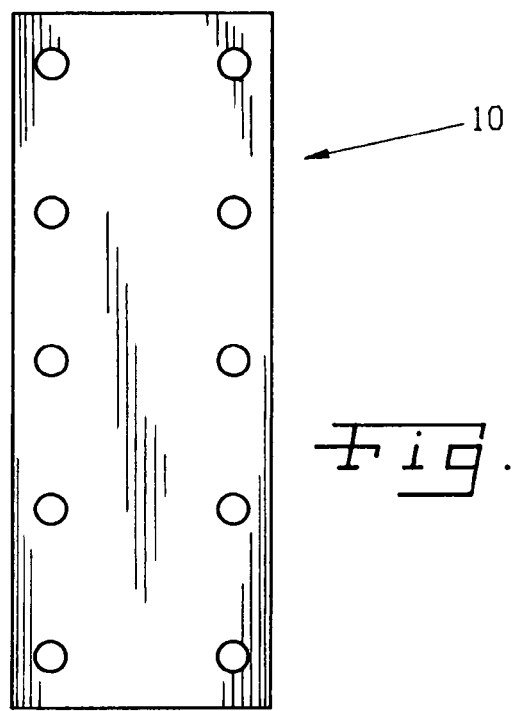
FIG. 1 is a planar diagrammatic view of a submucosa mesh, according to one form of the invention.
Figure 2:
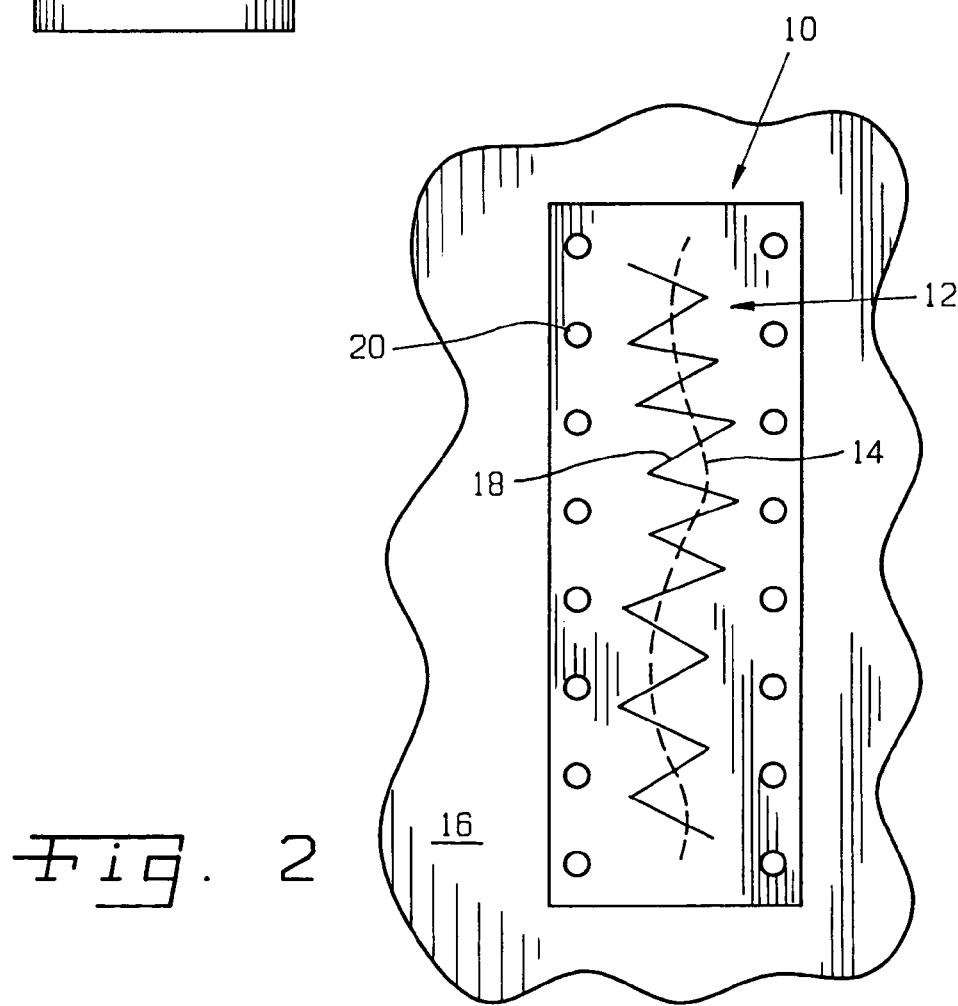
FIG. 2 is a planar diagrammatic view illustrating the use of the submucosa mesh of FIG. 1 in an incisional abdominal closure application to prevent incisional hernias, according to another form of the invention.

Referring now to the drawings and particularly to FIG. 1, there is shown in illustrative depiction a submucosal mesh 10 that constitutes, in various alternate forms, a tissue graft composition, material, article and/or construct, according to one form of the invention. Reference is also made to FIG. 2, which illustrates the use of mesh 10 in a surgical procedure, namely, an abdominal closure routine, according to another form of the invention.

Referring to FIG. 1, submucosa mesh 10 is formed by any suitable means known to those skilled in the art. For example, mesh 10 will possess properties upon fabrication that enable it to be biocompatible with an internal human environment, namely, suitable for permanent implantation and use at internal sites of the body.

The geometry of mesh 10 will be tailored to the intended application and surgical environment. Accordingly, although mesh 10 is shown in a generally rectangular form, this depiction is for illustrative purposes only and should not be considered in limitation of the invention, as it should be apparent to those skilled in the art that any other suitable size, shape and form can be used depending upon the specifications of the surgical routine. Mesh 10, in alternate forms, can be considered a solid body tissue structure (e.g., three-dimensional) having a dimensional profile suited to the intended application. For example, in some applications, it may be desirable to provide mesh 10 as a relatively thin sheath-type construct formed as a planar-type tissue sheet. It may also be desirable to provide mesh 10 in a relatively small form such as a patch-type construction to facilitate multiple placements of mesh 10 at various targeted sites, e.g., several incision sites.

Alternately, for uses such as reconstruction or replacement of an organ or other anatomical or physiological entity or structure, it may be necessary to provide mesh 10 in a form that resembles or models the targeted anatomical entity in a template-type manner. For example, mesh 10 can be constituted as a substrate or host structure that replaces, in whole or in part, the target body part. For this purpose, mesh 10 will be suitably formed in a manner known to those skilled in the art that enables mesh 10 upon implantation to readily assimilate, incorporate, and otherwise integrate into the internal environment. Additionally, in a reconstruction or replacement applications, mesh 10 will be fashioned to substantially duplicate as much as practicable the functional and structural aspects of the replaced body part. In essence, mesh 10 will serve as an effective functional equivalent of the replaced target body part.

Mesh 10 can also be constituted as a multi-piece construction that is formed, for example, from multiple submucosa tissue sheets integrated together to form a cohesive multi-layered, multi-laminate or multi-tiered construct.

It should be apparent that mesh 10 can be readily conditioned, treated and/or processed to make it suitable for use at internal body sites, according to conventional means known to those skilled in the art. Furthermore, mesh 10 will be formed to possess chemical, biological, mechanical, and/or physiological properties and characteristics that promote its integrity, durability, and functionality upon its implantation or placement in the body.

In one alternate form, mesh 10 can be constituted as a small intestine submucosa (SIS) construct. For example, the SIS construct can be formed from submucosa of a warm-blooded vertebrate, wherein the submucosa is delaminated from both the external smooth muscle layers and the luminal portions of the tunica mucosa. In one form, the submucosa comprises tunica submucosa delaminated from both the tunica muscularis and at least the luminal portion of the tunica mucosa of vertebrate intestinal tissue.

In various forms, depending upon the application, the SIS constructs discussed herein can be considered to constitute, without limitation, artificial organ or tissue constructs; prosthetic structures; implantable articles; incisional closure mechanisms; suturing mechanisms; and/or a remodeling template for the ingrowth of patient cells.

The functional uses of the SIS constructs discussed herein can be considered to include, but is not limited to, the prevention of incisional hernias; the repair of hernia defects; general suturing; the repair, replacement or reconstruction of damaged or diseased or non-functioning tissues, organs, or physiological units or parts; the treatment of patients with diseased or damaged organs or tissues; tissue or organ augmentation; promoting endogenous regrowth and healing of damaged or diseased tissues; and/or tissue or organ substitution.

Among its various aspects, the submucosa constructs discussed herein may exhibit material and functional properties including, without limitation, resorbable, remodelable, implantable, and/or biocompatible capacities.

Additional disclosures of submucosa technology may be found in the following U.S. patent documents, each incorporated herein by reference thereto: U.S. Pat. No. 6,241,981 Composition and Method for Repairing Neurological Tissue; U.S. Pat. No. 6,176,880 Tissue Graft Construct for Replacement of Cartilaginous Structures; U.S. Pat. No. 6,096,347 Myocardial Graft Constructs; U.S. Pat. No. 5,641,518 Method of Repairing Bone Tissue; U.S. Pat. No. 5,445,833 Tendon or Ligament Graft for Promoting Autogenous Tissue Growth; U.S. Pat. No. 5,372,821 Graft for Promoting Autogenous Tissue Growth; U.S. Pat. No. 6,113,623 Prosthetic Device and Method for Eventration Repair; U.S. Pat. No. 5,743,917 Prosthesis for the Repair of Soft Tissue Defects; U.S. Pat. No. 5,725,577 Prosthesis for the Repair of Soft Tissue Defects; U.S. Pat. No. 6,391,538 Stabilization of Implantable Bioprosthetic Tissue; U.S. Pat. No. 6,334,872 Method for Treating Diseased or Damaged Organs;

U.S. Pat. No. 6,334,446 Medical Sling Procedures and Anchor Insertion Methods and Devices; U.S. Pat. No. 6,312,474 Resorbable Implant Materials; U.S. Pat. No. 6,171,344 Bladder Submucosa Seeded with Cells for Tissue Reconstruction; U.S. Pat. No. 5,733,337 Tissue Repair Fabric; U.S. Pat. No. 5,352,463 Tissue Graft for Surgical Reconstruction of a Collagenous Meniscus and Method Therefor; U.S. Pat. No. 5,275,826 Fluidized Intestinal Submucosa and its Use as an Injectable Tissue Graft; U.S. Pat. No. 6,485,723 Enhanced Submucosal Tissue Graft Constructs; U.S. Pat. No. 6,375,989 Submucosa Extracts; U.S. Pat. No. 6,099,567 Stomach Submucosa Derived Tissue Graft; U.S. Pat. No. 5,997,575 Perforated Submucosal Tissue Graft Constructs; U.S. Pat. No. 5,968,096 Method of Repairing Perforated Submucosal Tissue Graft Constructs; U.S. Pat. No. 5,762,966 Tissue Graft and Method for Urinary Tract Urothelium Reconstruction and Replacement; U.S. Pat. No. 5,755,791 Perforated Submucosal Tissue Graft Constructs; U.S. Pat. No. 5,554,389 Urinary Bladder Submucosa Derived Tissue Graft; U.S. Pat. No. 5,516,533 Fluidized Intestinal Submucosa and its Use as an Injectable Tissue Graft; U.S. Pat. No. 4,956,178 Tissue Graft Composition; U.S. Pat. No. 4,902,508 Tissue Graft Composition; and U.S. Pat. No. 5,711,969 Large Area Submucosal Tissue Graft Constructs.

Referring now to FIG. 2, there is shown an illustrative surgical configuration of mesh 10 in which mesh 10 is placed in effective proximal juxtaposition to an illustrative abdominal incision 12 during an abdominal closure routine, according to another form of the invention. As shown, mesh 10 has been applied by suitable surgical means to close or otherwise facilitate and/or assist in the closure of the abdominal incision 12. As discussed below, the illustrated use of mesh 10 is especially provided as preventative care to prevent, oppose, or counter the occurrence or incidence of incisional hernias stemming from herniation via incision 12.

In alternate forms, it should be considered that incision 12 is merely representative of any breach in the abdominal wall anatomy and is not limited to incisional-type openings such as depicted in FIG. 2. Accordingly, the invention can be practiced with equal effectiveness to close any breach in the abdominal wall, whether from an incision or otherwise from other causes.

In alternate forms, mesh 10 can be used to reinforce an existing conventional incisional suture or can serve as the entire and sole abdominal incision closure mechanism. In one advantage of the invention, the use of mesh 10 can be readily incorporated into the normal and conventional abdominal closure routine as a primary or supplemental/secondary suturing or closure protocol. It should be apparent that the invention can be practiced in any surgical, medical or operating application where an abdominal incision has been made or otherwise when abdominal closure is indicated. For example, the invention can be practiced in surgical environments where abdominal closure is indicated due to non-incisional breaches of the abdominal wall or anatomy. For example, as discussed further, the invention can be applied to the repair of both incisional and non-incisional hernia defects.

Referring again to FIG. 2, incision 12 is shown with now-closed incision line 14 made in an anatomical or physiological entity 16 (shown in fragmented form), such as the abdominal wall. As shown, exemplary sutures 18 have been incorporated to surgically close and/or seal incision 12, in a manner known to those skilled in the art and particularly in accordance with well known surgical routines and specifications.

According to the invention, submucosa mesh 10 is disposed in overlying covering relationship to incision 12 or otherwise applied to incision 12 in a manner that fosters or promotes integrity of the abdominal wall closure, e.g., retention and stability of sutures 18. The extent of the coverage of incision 12 afforded by the superimposition of mesh 10 may take on any of various forms. For example, while it is preferred that mesh 10 completely cover incision 12, partial coverage is also possible.

The installed, implanted, or working relationship of mesh 10 to incision 12 is preferably characterized by a contacting relationship between the submucosal tissue of mesh 10 and at least the portion of the abdominal wall 16 at and around incision 12. Preferably, the entire side of mesh 10 facing incision 12 (e.g., the application side) forms a surface-to-surface contacting relationship with the anatomical surface of the abdominal wall in direct opposition thereto. In this manner, the submucosal tissue of mesh 10 is absorbed or otherwise assimilated into the physiological structure of the abdominal wall and becomes an effective functional portion thereof.

It should be apparent that the construction and application of mesh 10 to incision 12 is made with a view towards accomplishing or otherwise facilitating, promoting, or fostering abdominal wall closure. Accordingly, to achieve this end, any conventional surgical procedures and techniques known to those skilled in the art may be used to incorporate or otherwise deploy mesh 10 into the body at incision 12.

In alternate forms, a surgical procedure may be developed that deploys mesh 10 into the body at incision 12 as the primary suturing mechanism, namely, without the use of suture threads 18. Conventional surgical methods may be used to prepare incision 12 for singular closure by the use of mesh 10.

Although a single mesh 10 is shown in FIG. 2, this depiction should not be considered in limitation of the invention, as any arrangement of such meshes 10 may be employed. In one configuration, a series of individual meshes 10 may be applied in succession to the incision area to form a hierarchical or layered arrangement exhibiting a sequence of reinforcing structures. For example, working from the incision level outwards, a succession of individual meshes 10 in increasing size may be applied in overlying relationship to each other. To add further support, additional meshes 10 may also be used around the periphery of incision 12 in overlapping relationship to the central mesh 10 that covers incision 12.

Any conventional means known to those skilled in the art may be used to unite, join, attach, or otherwise secure mesh 10 to abdominal wall 16. For example, as shown, mesh 10 is provided with an exemplary set of perforations or holes 20 formed about its periphery to facilitate suturing attachment to abdominal wall 16. Any number, arrangement and size of perforations 20 may be used to facilitate the attachment of mesh 10. Mesh 10 may also be attached by sutureless means.

It should also be apparent that the size and shape of mesh 10 is adapted or otherwise accommodated to fit over incision 12 in a manner promoting abdominal wall closure. Incision 12 may also be closed or covered by a set of smaller individual submucosa mesh components that are arranged serially along incision 12 in abutting or overlapping relationship, for example. In this manner, if one mesh component fails or weakens, other ones of the mesh components may continue to provide independent support to the abdominal incision closure.

One advantageous feature of deploying mesh 10 in the surgical environment of FIG. 2 is that it prevents or at least resists or inhibits the occurrence or formation of an incisional hernia at the incision site 12. By applying mesh 10 to incision 12, a measure of support is added to the abdominal closure that is not otherwise available by the traditional use of normal sutures 18. Since the submucosa mesh 10 eventually biologically fuses to and/or is absorbed into the surrounding anatomical area to which it is initially attached (e.g., the endogenous abdominal wall tissue structure), the integrity and strength of the as-absorbed mesh 10 will be commensurate with the intact abdominal wall, which in most cases will be more that sufficient to hold together, support and stabilize the abdominal wall closure.

In a typical incisional hernia, a precipitating event causes the abdominal wall closure to be breached. A scenario for an incisional hernia typically exhibits some disruption to the stability of the sutures 18 that allows the abdominal incision to reopen. For example, the sutures 18 may be torn from their anchoring positions or a new tear in the abdominal wall may propagate from the ends of the original incision. Whatever the cause, the integrity of the sutured closure is compromised during an incisional hernia.

However, in the invention, the submucosa mesh construct is incorporated into the routine surgical abdominal wall closure in a manner that is effective to at least mitigates the occurrence or recurrence of an incisional hernia. Unlike traditional scenarios where compromise of the closure sutures can lead to incisional hernias, a breach in the submucosa mesh of the invention would also have to occur to initiate an incisional hernia. However, the comparatively higher strength and stability of the submucosa mesh relative to traditional sutures significantly improves the integrity and durability of the abdominal closure, particularly in regard to hernia incipience, onset, and incidence.

According to various functional characterizations, the submucosal mesh 10 can be considered to support the abdominal closure and/or maintain, preserve, and sustain the abdominal closure.

Although the surgical technique shown in FIG. 2 is discussed in relation to abdominal closure protocols, it should be considered that the invention can be practiced with incisional closure routines affecting anatomical entities other than the abdominal wall.

Figure 3:
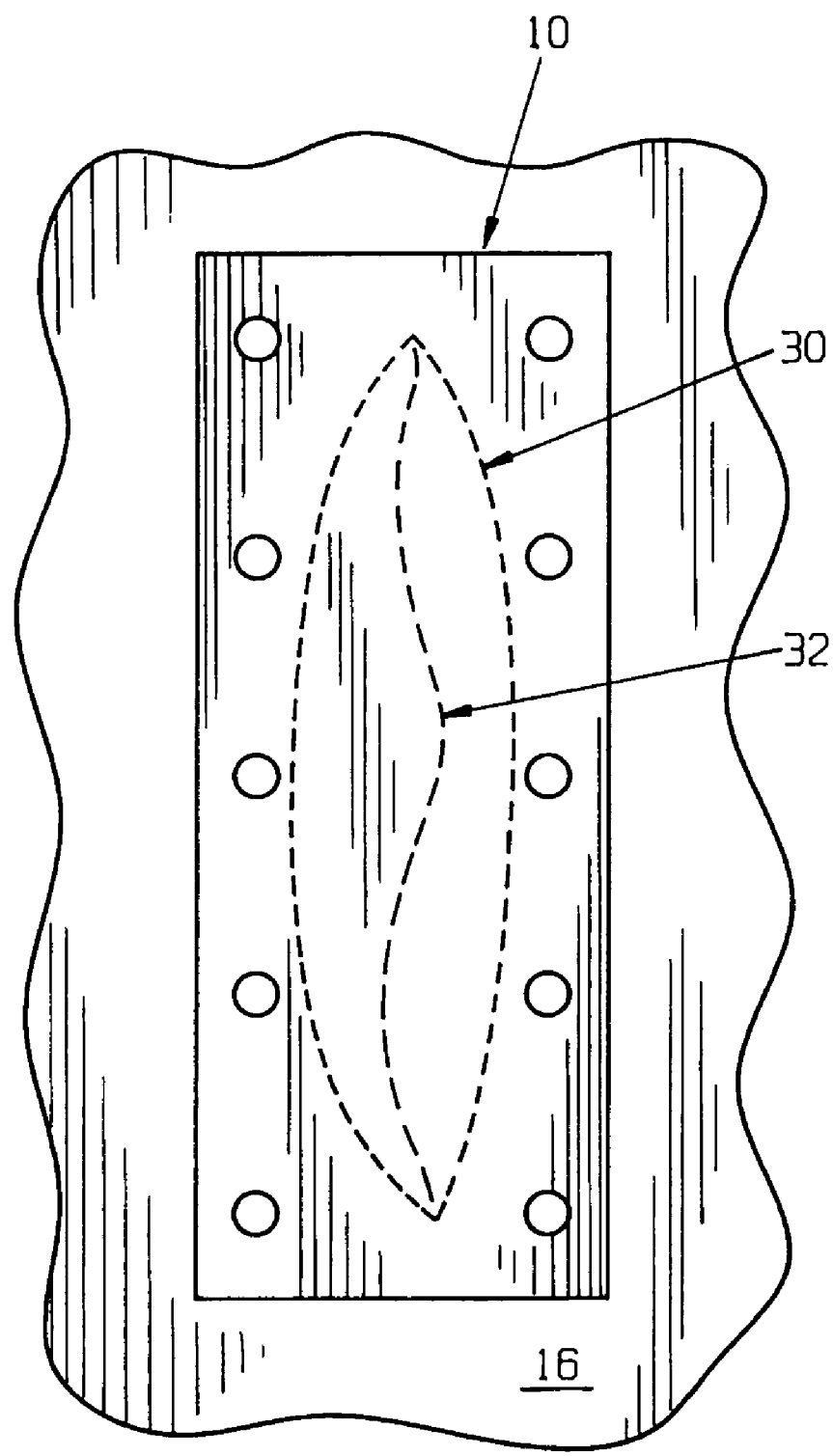
FIG. 3 is a planar diagrammatic view illustrating the use of the submucosa mesh of FIG. 1 in an abdominal closure application to repair a hernia defect, according to another form of the invention.

Referring now to FIG. 3, there is shown an illustrative surgical configuration of mesh 10 deployed in the manner shown to repair a hernia defect (generally depicted at 30), according to another form of the invention.

As shown, mesh 10 has been applied by suitable surgical means to repair hernia defect 30, e.g., to close or otherwise facilitate the closure of the hernia-type breach or opening. For comparison purposes, the untreated hernia defect is depicted generally in exaggerated view by breach or opening 30 (prior to the use of mesh 10), while the abdominal closure line subsequent to practice of the invention is depicted generally at 32 to illustrate how hernia defect 30 is treated (e.g., closed) by the use of mesh 10. As discussed below, the illustrated use of mesh 10 is especially suited as a repair mechanism to repair abdominal wall hernias.

It should be considered that the surgical abdominal closure technique illustrated by FIG. 3 can be employed in connection with any type of hernia defect, regardless of cause and/or origin. For example, the illustrated surgical technique can be used in connection with incisional or non-incisional hernias and with any type of hernia, including, but not limited to, abdominal and inguinal.

The manner and aspects of applying submucosa mesh 10 to hernia defect 30 to produce abdominal closure 32 is similar to the manner in which mesh 10 is applied to incision 12 in FIG. 2. In all other respects, the surgical technique illustrated by FIG. 3 is similar to conventional procedures known to those skilled in the art for surgically treating and addressing hernia defects. For example, although not shown, sutures may be used to initially close hernia defect 30, followed by deployment and implantation of mesh 10. Optionally, the abdominal closure 32 may be realized without the use of such sutures, in which mesh 10 singularly provides the suturing support sufficient to accomplish repair or closure of the hernia defect.

Figure 4:
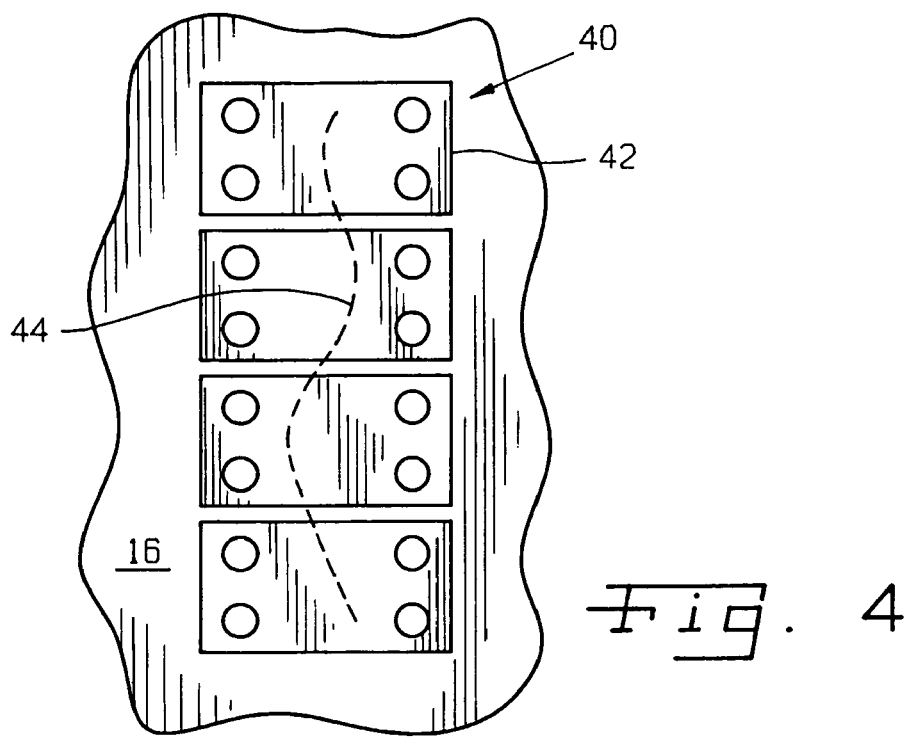
FIG. 4 is a planar diagrammatic view illustrating the use of submucosa patch elements as suturing components, according to another form of the invention.

Referring now to FIG. 4, there is shown a matrix or network 40 of individual discrete submucosa patch elements 42 arranged and adapted as suturing components to cooperatively provide a suture-type closure (depicted generally at 44), according to another form of the invention.

In one form, submucosa patch elements 42 are constituted as compact or subcompact versions of the submucosa mesh 10 in FIG. 1. Accordingly, the manner, feature and aspects of making and forming patch 42 is similar to mesh 10, as discussed above. The arrangement of patch elements 42 may be used to define the suturing or closure mechanism in any surgical application. For example, the patch elements 42 may be used as a replacement for conventional threaded sutures employed to close an incision, hernia defect, or other unwanted breach or opening. Additionally, patch elements 42 may be used in conjunction with any anatomical site, including, but not limited to, abdominal wall closures.

Figure 5:
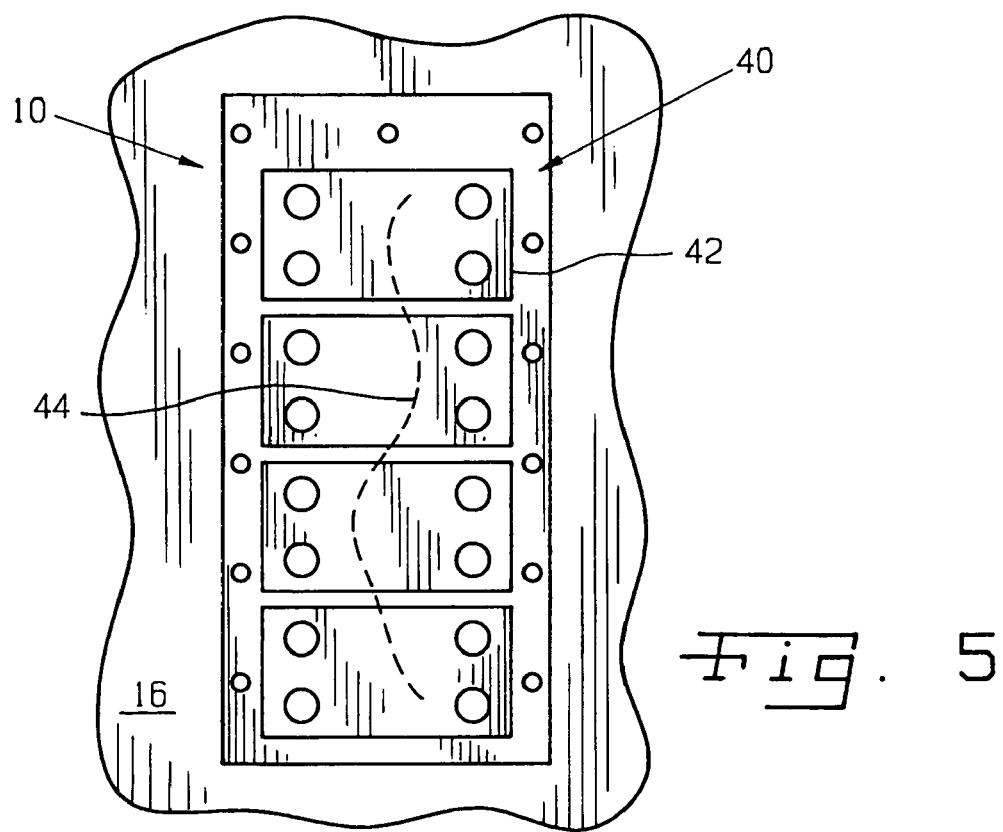
FIG. 5 is a planar diagrammatic view illustrating a combination including the submucosa mesh of FIG. 1 and the submucosa patch elements of FIG. 4 for use in a surgical application, according to another form of the invention.

In one advantageous feature, the patch elements 42 may be used in combination with mesh 10 (FIG. 1) to constitute an entirely submucosa-based or submucosa-derived construct assembly capable of providing the following functionalities: (i) suturing the abdominal opening with patch elements 42, and (ii) supporting the sutured abdominal closure with mesh 10. FIG. 5 illustrates an exemplary configuration that employs such a combination.

In one form, the submucosa patch elements 42 may be considered bioretention sutures, which preferably take the place of external retention sutures currently in use. The advantage of such internal submucosa retention sutures is that these tissue components are reabsorbed into the host or carrier site which accepts patch elements 42 (e.g., abdominal wall), and therefore do not have to be removed like external sutures.

Additionally, internal bioretention sutures provide long-term strength since they remain fully intact and permanently resident within the body. The added strength is notably apparent and beneficial to fascial closures.

Current retention sutures are very painful to the patient since they are external and therefore tend to pull on the abdominal wall.

Additionally, external sutures tend to dig into the skin and thereby cause irritation, infection, and unsightly scars. However, the internal bioretention sutures of the invention exhibit none of these problems. Furthermore, as compared to external sutures that are eventually removed, the implanted internal bioretention sutures provide continuous added strength, particularly to abdominal wall closures where elevated stresses and strains can occur that weaken traditional sutured closures and make the area vulnerable or susceptible to herniation.

According to another form of the invention, the submucosa construct can be adapted for use as part of a surgical strategy to facilitate wound healing or treatment, regeneration, support, reconstruction, and replacement of anatomical structures, such as tissues and organs, without any loss or diminution in mechanical functionality, kinematic capabilities, or other functional or biological properties.

For example, the submucosa constructs discussed herein can be adapted in any suitable manner to form a scaffold-type article that serves as a platform for substitution in the anatomy. For example, the submucosa construct can replace in whole or in part an organ or other structure of the body. The replacement strategy, for example, can be devised to replace damaged or diseased structures. The construct can also be adapted to facilitate regeneration and synthesis with the surrounding anatomical environment.

Suitable means known to those skilled in the art can be employed to fashion the replacement or substitute submucosa construct, such as in accordance with the functional and structural specifications of the target environment or destination in the body. For example, the construct can be formed entirely of submucosa, or combined with any number of diverse elements, such as synthetic and natural materials to enhance the regrowth, synthesis, and physiological/biological acceptance of the introduced construct.

By way of background, in regard to the acquisition and preparation of the submucosal tissue constructs/articles, the invention as discussed herein is directed to a tissue graft composition (e.g., mesh 10) comprising primarily the tunica submucosa of a segment of small intestine of a warm-blooded vertebrate. The tunica submucosa is delaminated from the tunica muscularis and at least the luminal portion of the tunica mucosa of the section of small intestine. The present tissue graft composition exhibits excellent functional characteristics in various graft applications, including, but not limited to, autografts, allografts, heterografts, homografts, and xenografts.

The tissue graft composition exhibits multiple physical and biological characteristics that renders it particularly adapted for tissue graft applications.

In one form, the tissue graft material comprises submucosa tissue and basilar mucosa tissue delaminated from a segment of the small intestine, more preferably the jejunum, a division of the small intestine extending between the duodenum and the ileum. The small intestine, prior to its manipulation (delamination) to yield graft material in accordance with this invention, is made up of a number of discrete tissue layers defining the intestinal wall. The outermost tissue layer is the mesenteric tissues. The next successive layers are the tunica serosa and the tunica muscularis, respectively. The next layer, the tunica submucosa, is a dense, irregular collagenous connective tissue often harboring numerous mast cells.

The next set of tissue layers collectively represent the so-called tunica mucosa. The first layer of the tunica mucosa is a layer of smooth muscle cells known as the lamina muscularis mucosa. The next layer, the stratum compactum, consists of acellular collagen and elastin fibers. The next layer consists of the lamina epithelialis mucosa and its lamina propria, which together and arranged in villous processes, a series of finger-like outgrowths of the mucous membrane.

Following the below-detailed manipulation of the intestinal tissue segment to prepare the graft material of this invention, histologic examination reveals that the lamina epithelialis mucosa and its lamina propria have been removed, as have the tunica muscularis and the tunica serosa. In one form, the graft material of this invention thus comprises the tunica submucosa, along with basilar portions of the tunica mucosa, particularly the lamina muscularis mucosa and the stratum compactum. Those layers collectively are referred to as the Small Intestine Submucosa ("SIS").

An SIS autograft in accordance this invention can be prepared, for example, by first resecting a segment of autogeneous proximal jejunum following a midline laparotomy incision. The resected segment of jejunum is then wrapped in surgical sponges which have been soaked in physiologic saline. Upon completion of the intestinal anastomosis, the excised intestinal segment is prepared in accordance with the hereinafter described method for use as a tissue graft material. Similarly, allografts are prepared from intestinal tissue removed from organ/tissue donors of the same species. Heterografts can be prepared, for example, from feline, porcine, or bovine intestinal tissue retrieved from euthanized animals at slaughterhouse operations. For example, pig intestine can be harvested. To date, minimal morphological differences have been found in intestinal tissues from different species.

In one exemplary protocol, the tissue graft material of this invention is prepared by abrading intestinal tissue to remove the outer layers including both the tunica serosa and the tunica muscularis and the inner layers including at least the luminal portion of the tunica mucosa. Under conditions of mild abrasion the tunica mucosa is delaminated between the stratum compactum and the lamina propria. More particularly, following removal of any mesenteric tissues from the intestinal segment utilizing, for example, Adson-Brown forceps and Metzenbaum scissors, the tunica serosa and the tunica muscularis (the outer tissue layers) are delaminated from the intestinal segment by abrasion using a longitudinal wiping motion with a scalpel handle and moistened gauze.

Following eversion of the intestinal segment, the luminal portion of the tunica mucosa is delaminated from the underlying tissue using the same wiping motion. Care is taken to prevent perforation of the submucosa. Optionally, the intestinal segment may be everted first, then stripped of the luminal layers, then reinserted to its original orientation for removal of the tunica serosa and the tunica muscularis. The graft material is a whitish, translucent tube of tissue approximately 0.1 mm thick (although other suitable thicknesses are possible), typically consisting of the tunica submucosa with the attached lamina muscularis mucosa and stratum compactum. For graft preparation, for example, the prepared graft may be everted to its original orientation so that the stratum compactum serves as the luminal surface of the graft.

The prepared graft material is typically rinsed with saline and placed in a 10% neomycin sulfate solution for approximately 20 minutes, after which time the graft material is ready for use. The grafts are applied using routine surgical procedures commonly employed for tissue graft applications. For use in tissue graft applications, the tubular graft material can be cut longitudinally and rolled out to form a "patch" of tissue.

Indeed, the entire tissue delamination procedure described above can be carried out on "patches" of intestinal tissue prepared by cutting the intestinal segment longitudinally and "unrolling" it to form a pre-graft patch. The prepared graft tissue patches can be utilized, for example, as a graft material or for repair of other body tissue defects lending themselves to surgical application of a tissue graft patch having the physical and functional characteristics of the present graft composition.

Consistent with the objects of this invention, the SIS composition possesses mechanical properties highly desirable for tissue graft materials, including low porosity index, high compliance, and a high burst pressure point. As for porosity, one skilled in the art will appreciate that tissue graft material must be of low enough porosity to prevent intraoperative hemorrhage and yet of high enough porosity to allow extension of a newly-developed vasa vasorum through the graft material to nourish the neointima and luminal surface.

Regarding graft compliance, there has been described in the art the existence of a direct relationship between compliance and patency. Ideally the graft material herein should be at least as compliant as the tissue it replaces.

In alternate forms, the formation of tissue graft constructs herein comprises large area sheets of submucosal tissue. The fabrication comprises the steps of fusing multiple strips of submucosal tissue to form unitary heterolaminar, and optionally multi-ply sheets of submucosal tissue.

Furthermore, in other forms, the submucosal tissue suitable for use in the formation of the present graft constructs comprises naturally associated extracellular matrix proteins, glycoproteins and other factors. One source of submucosal tissue is the intestinal tissue of a warm-blooded vertebrate. Small intestinal tissue is a preferred source of submucosal tissue for use in this invention.

Suitable intestinal submucosal tissue typically comprises the tunica submucosa delaminated from both the tunica muscularis and at least the luminal portion of the tunica mucosa. In one form, the intestinal submucosal tissue comprises the tunica submucosa and basilar portions of the tunica mucosa including the lamina muscularis mucosa and the stratum compactum which layers are known to vary in thickness and in definition dependent on the source vertebrate species.

Generally, the preparation of submucosal tissue for use in accordance with this invention involves a segment of vertebrate intestine, such as harvested from porcine, ovine or bovine species, but not excluding other species, that is subjected to abrasion using a longitudinal wiping motion to remove the outer layers, comprising smooth muscle tissues, and the innermost layer, i.e., the luminal portion of the tunica mucosa. A similar procedure can be used to prepare submucosa tissue from urinary bladder. The submucosal tissue is rinsed with saline and optionally sterilized; it can be stored in a hydrated or dehydrated state. Lyophilized or air dried submucosa tissue can be rehydrated and used in accordance with this invention without significant loss of its biotropic and mechanical properties.

In another form, large area compliant sheets of submucosal tissue are formed from multiple partially overlapped strips of submucosal tissue. The dimensions of the individual strips of submucosal tissue used is not critical and the term "strip of submucosal tissue" is defined herein to include submucosal tissue from one or more vertebrate sources or organs in a wide variety of sizes and shapes. The amount of tissue overlap between the adjacent strips of submucosal tissue can be varied based on the intended use and the desired properties of the large area graft construct, provided that at least a portion of each strip of submucosal tissue overlaps with a portion of another strip of submucosal tissue. The strips of submucosal tissue are fused to one another along the overlapped portions, producing a compliant unitary heterolaminar sheet of submucosal tissue. The term "heterolaminar" as used herein refers to the variability in the number of layers of submucosa superimposed at (and fused) at different points on the unitary graft construct. The heterolaminar structure of the present graft constructs, especially in multi-ply constructs, provides enhanced mechanical strength.

Submucosal tissue typically has an abluminal and a luminal surface. The luminal surface is the submucosal surface facing the lumen of the organ source and typically adjacent to an inner mucosa layer in vivo whereas the abluminal surface is the submucosal surface facing away from the lumen of the organ source and typically in contact with smooth muscle tissue in vivo. The multiple strips of submucosal tissue can be overlapped with the abluminal surface contacting the luminal surface, the luminal surface contacting the luminal surface or with the abluminal surface contacting the abluminal surface of an adjacent strip of submucosal tissue. All of these combinations of overlapping strips of submucosal tissue from some or different vertebrate or organ sources will produce a large area sheet of submucosal tissue.

Notwithstanding the above, it should be apparent that the submucosal tissue composition disclosed herein can be acquired, prepared, derived, manufactured, processed, treated, conditioned, and otherwise supplied according to other means and processes known to those skilled in the art. Accordingly, the above description of the manufacture of the submucosal tissue is illustrative and should not be considered in limitation of the invention.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of promoting the maintenance of an incisional abdominal wall closure, said method comprising:
   creating an incision in an abdominal wall of a patient in conjunction with a surgical procedure;
   inserting closure sutures in the incision so as to close the incision;
   providing a tissue graft construct comprising naturally associated extracellular matrix proteins in a position spanning across the incision in the abdominal wall; and
   attaching the tissue graft construct to tissue of the patient so as to provide support to the closure sutures and thereby resist herniation of the incision, wherein said attaching comprises suturing.

2. A method of promoting the maintenance of an incisional abdominal wall closure, said method comprising:
   creating an incision in an abdominal wall of a patient in conjunction with a surgical procedure;
   inserting closure sutures in the incision so as to close the incision;
   providing a tissue graft construct comprising naturally associated extracellular matrix proteins in a position spanning across the incision in the abdominal wall; and
   attaching the tissue graft construct to tissue of the patient so as to provide support to the closure sutures and thereby resist herniation of the incision, wherein said tissue graft construct comprises a plurality of suture holes, and wherein said suturing comprises passing sutures through said suture holes.

* * * * *